United States Patent [19]
Schönherr et al.

[11] Patent Number: 5,981,798
[45] Date of Patent: Nov. 9, 1999

[54] PREPARATION OF A CRYSTALLINE SOLID FROM GLYCINE-N,N-DIACETIC ACID DERIVATIVES WITH SUFFICIENTLY LOW HYGROSCOPICITY

[75] Inventors: Michael Schönherr, Frankenthal; Matthias Rauls, Limburgerhof; Hermann Ascherl, Dirmstein; Thomas Letzelter, Annweiler; Dieter Baumann, Frankenthal; Birgit Potthoff-Karl, Ludwigshafen, all of Germany

[73] Assignee: BASF Aktiengesellschaft, Ludwigshafen, Germany

[21] Appl. No.: 08/964,755

[22] Filed: Nov. 5, 1997

[30] Foreign Application Priority Data

Nov. 29, 1996 [DE] Germany .............................. 196 49 681

[51] Int. Cl.⁶ .......................... C07C 51/42; C07C 229/00
[52] U.S. Cl. ............................. 562/593; 562/571
[58] Field of Search ...................... 562/571, 593

[56] References Cited

U.S. PATENT DOCUMENTS 3,932,316  1/1976  Sagel et al. .
3,956,379  5/1976  Beaver .

FOREIGN PATENT DOCUMENTS 2 024 203   1/1980   United Kingdom .
WO 94/29421 12/1994  WIPO .

OTHER PUBLICATIONS

Irving et al., J. Chem. Soc. A, <1966>, 1268–1275, Feb. 1966.

Korman et al., J. Biol. Chem., 221 <1956> 113, 119, Dec. 1955.

*Primary Examiner*—Paul J. Killos
*Assistant Examiner*—J. Parsa
*Attorney, Agent, or Firm*—Oblon, Spivak, McClelland, Maier & Neustadt, P.C.

[57] ABSTRACT

A crystalline solid which has a sufficiently low hygroscopicity for processing and use and essentially consists of glycine-N,N-diacetic acid derivatives is prepared by adjusting the water content of the starting material containing the glycine-N,N-diacetic acid derivatives to a value of from 10 to 30% by weight, based on the starting material, and subsequently bringing about crystallization.

7 Claims, No Drawings

PREPARATION OF A CRYSTALLINE SOLID FROM GLYCINE-N,N-DIACETIC ACID DERIVATIVES WITH SUFFICIENTLY LOW HYGROSCOPICITY

Complexing agents for alkaline earth and heavy metal ions employed, for example, in detergents and cleaners are customarily synthesized in aqueous solution. For certain applications they are required in solid form.

Customary processes for preparing solids from solutions are, in particular, crystallization and spray-drying processes. It is known that crystalline solid resulting, for example, from evaporation or cold crystallization processes may contain water of crystallization and, under ambient conditions, is usually less hygroscopic and more stable on storage than amorphous solid. Spray-drying processes (eg. in a spray tower or spray fluidized bed) by contrast result in an amorphous solid. In this form, the solid is often highly hygroscopic and, on open storage under ambient conditions, its flowability is lost within a short time. This is why measures for increasing the storage stability of spray powders are described in the literature, eg. compaction or after-treatment with builders for detergents with benzoic acid in U.S. Pat. No. 3,932,316.

WO-A-94/29421 discloses glycine-N,N-diacetic acid derivatives as complexing agents for alkaline earth and heavy metal ions in a wide variety of industrial applications. Crystallization of these glycine-N,N-diacetic acid derivatives, eg. α-alanine-N,N-diacetic acid in the form of the trisodium salt, is greatly inhibited so that conventional crystallization processes are impossible or uneconomic. After-treatment of amorphous spray powder of these compounds with additives, eg. benzoic acid as disclosed in U.S. Pat. No. 3,932,316, is unwanted for some applications and is also able to improve the storage stability to only a limited extent. The stability does not reach that of a crystalline solid.

It is an object of the present invention to provide a virtually nonhygroscopic, stable, crystalline solid essentially from glycine-N,N-diacetic acid derivatives which is substantially free of additives.

We have found that this object is achieved by a process for preparing a crystalline solid which has a sufficiently low hygroscopicity for processing and use and essentially consists of glycine-N,N-diacetic acid derivatives of the formula I

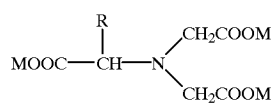

(I)

where

R is $C_1$–$C_{30}$-alkyl or $C_2$–$C_{30}$-alkenyl, each of which may additionally be substituted by up to 5 hydroxyl groups, formyl groups, $C_1$–$C_4$-alkoxy groups, phenoxy groups or $C_1$–$C_4$-alkoxy-carbonyl groups and be interrupted by up to 5 nonadjacent oxygen atoms, alkoxylate groups of the formula

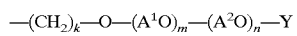

where $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3, and m and n are each from 0 to 50, where the total of m+n must be at least 4, phenylalkyl groups having 1 to 20 carbon atoms in the alkyl, a five- or six-membered unsaturated or saturated heterocyclic ring which has up to three heteroatoms from the group of nitrogen, oxygen and sulfur and may additionally be benzo-fused, it being possible for all the phenyl nuclei and heterocyclic rings mentioned for the meanings of R additionally to be substituted by up to three $C_1$–$C_4$-alkyl groups, hydroxyl groups, carboxyl groups, sulfo groups or $C_1$–$C_4$-alkoxycarbonyl groups, or a radical of the formula

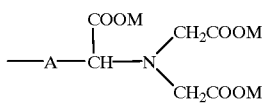

where A is a $C_1$–$C_{12}$-alkylene bridge or a chemical bond, and

M is hydrogen, alkali metal, alkaline earth metal, ammonium or substituted ammonium in the appropriate stoichiometric amounts, which comprises adjusting the water content of the starting material containing the glycine-N,N-diacetic acid derivatives I to a value of from 10 to 30% by weight, based on the starting material, and subsequently bringing about crystallization.

In this connection, a solid is referred to as nonhygroscopic or of sufficiently low hygroscopicity if, on open storage under normal ambient conditions, eg. 25° C. and a relative humidity of 76%, it retains its consistency as flowable powder or granules over a period of at least one week.

The crystalline solid prepared according to the invention essentially consists of compounds I, ie. small amounts of starting materials and/or byproducts from the preparation of the glycine-N,N-diacetic acid derivatives I may also be present. Depending on the synthetic process used, compounds I normally have purities of from 70 to 99.9% by weight, in particular 80 to 99.5% by weight, in each case based on the solids content.

Adjustment of the water content of the starting material is particularly important for the preparation according to the invention of the crystalline solid. The water content must be chosen so that the crystallization can take place optimally, where appropriate with inclusion of water of crystallization. It is preferably from 15 to 25% by weight, in particular 18 to 22% by weight, this being determined by Karl Fischer titration.

In a preferred embodiment, the starting material used for the crystallization is produced by adjusting an appropriate aqueous solution of the glycine-N,N-diacetic acid derivatives I to the required water content by distilling off water ("evaporating").

In another preferred embodiment, the starting material with the required water content used for the crystallization is produced by mixing an appropriate aqueous solution of the glycine-N,N-diacetic acid derivatives I with dehydrated glycine-N,N-diacetic acid derivatives I in the suitable ratio.

In another preferred embodiment, the starting material with the required water content used for the crystallization is produced by mixing dehydrated glycine-N,N-diacetic acid derivatives I with water in the suitable ratio.

When dehydrated glycine-N,N-diacetic acid derivatives I are used, they have, as a rule, been prepared by conventional spray-drying processes and usually have a residual water content of from 0.1 to less than 10% by weight, in particular from 0.5 to 5% by eight.

It is adantageous to carry out production of the starting material described above and the subsequent crystallization in the same apparatus.

The crystallization converts the starting material under favorable conditions in a short time into a crystalline solid which complies with the requirements in respect of hygroscopicity, flowability and storability. It is therefore advantageous to carry out the crystallization in particular in a favorable temperature range, with addition of crystallization nuclei and/or with mechanical stress. The crystallization of the starting material then takes place in a few minutes.

The temperature of the crystallization is preferably adjusted to values in the range from 10 to 100° C., in particular from 20 to 90° C., especially from 40 to 80° C.

The crystallization is advantageously speeded up by adding from 0.001 to 50% by weight, preferably 0.01 to 10% by weight, based on the amount of glycine-N,N-diacetic acid derivatives I present in the starting material, of crystalline glycine-N,N-diacetic acid derivatives I as crystallization nuclei. In this connection, the deposits of product present in the crystallization apparatus from previous production batches are often sufficient as nuclei.

A mechanical stress with a beneficial effect can be brought about in particular by a suitable mixing, stirring, kneading or extrusion apparatus. It is advantageous to use an apparatus with compulsory cleaning, eg. a Discotherm reactor ("DTB"), so that no deposits build up during the crystallization process.

The crystallization is normally carried out without adding other solvents or diluents. In particular, the water content of the starting material is not altered during the crystallization.

The process according to the invention is preferably suitable for compounds I where R is $C_1$–$C_{20}$-alkyl, $C_2$–$C_{20}$-alkenyl or a radical of the formula

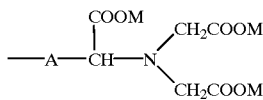

Particularly preferably employed as compound I are α-alanine-N,N-diacetic acid (R=CH$_3$) and its alkali metal, ammonium and substituted ammonium salts.

Particularly suitable salts of this type are the sodium, potassium and ammonium salts, especially the trisodium, tripotassium and triammonium salt, and organic triamine salts with a tertiary nitrogen atom.

Particularly suitable bases underlying the organic amine salts are tertiary amines such as trialkylamines having 1 to 4 carbon atoms in the alkyl, such as trimethyl- and triethylamine, and trialkanolamines having 2 or 3 carbon atoms in the alkanol residue, preferably triethanolamine, tri-n-propanolamine or triisopropanolamine.

Alkaline earth metal salts which are particularly employed are the calcium and magnesium salts.

Besides methyl, suitable straight-chain or branched alk (en)yl radicals for the radical R are, in particular, $C_2$–$C_{17}$-alkyl and -alkenyl, and of these in particular straight-chain radicals derived from saturated or unsaturated fatty acids. Examples of specific radicals R are: ethyl, n-propyl, isopropyl, n-butyl, isobutyl, sec-butyl, tert-butyl, n-pentyl, isopentyl, tert-pentyl, neopentyl, n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). Mixtures may also occur for R, especially those derived from naturally occurring fatty acids and from synthetic acids produced industrially, for example by the oxo synthesis.

$C_1$–$Cl_2$-Alkylene bridges A which are particularly used are polymethylene groups of the formula —(CH$_2$)$_k$— where k is from 2 to 12, in particular 2 to 8, ie. 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred in this connection. However, branched $C_1$–$C_{12}$-alkylene groups may also occur in addition, eg. —CH$_2$CH(CH$_3$)CH$_2$—, —H$_2$C(CH$_3$)$_2$CH$_2$—, —H$_2$CH(C$_2$H$_5$)— or —CH$_2$CH(CH$_3$)—.

The $C_1$–$C_{30}$-alkyl and $C_2$–$C_{30}$-alkenyl groups may have up to 5, in particular up to 3s additional substituents of the stated type and be interrupted by up to 5, in particular up to 3, nonadjacent oxygen atoms. Examples of such substituted alk(en)yl groups are —CH$_2$OH, —CH$_2$CH$_2$OH, —CH$_2$CH$_2$—O—CH$_3$, —CH$_2$CH$_2$—O—CH$_2$CH$_2$—O—CH$_3$, —CH$_2$—O—CH$_2$CH$_3$, —CH$_2$—O—CH$_2$CH$_2$—OH, —CH$_2$—CHO, —CH$_2$—OPh, —CH$_2$—COOCH$_3$ or —CH$_2$CH$_2$—COOCH$_3$.

Particularly suitable alkoxylate groups are those in which m and n are each from 0 to 30, in particular 0 to 15. $A^1$ and $A^2$ are groups derived from butylene oxide and, in particular, from propylene oxide and from ethylene oxide. Pure ethoxylates and pure propoxylates are of particular interest, but ethylene oxide/propylene oxide block structures may also occur.

Suitable five- or six-membered unsaturated or saturated heterocyclic rings having up to three heteroatoms from the group of nitrogen, oxygen and sulfur, which may additionally be benzofused and be substituted by the indicated radicals, are:

Tetrahydrofuran, furan, tetrahydrothiophene, thiophene, 2, 5-dimethyithiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2, 3- , 1,2,4- and 1,2,5-oxadiazole, tetrahydropyran, dihydropyran, 2H- and 4H-pyran, piperidine, 1,3- and 1,4-dioxane morpholine, pyrazan, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chroman, isochroman, 2H- and 4H-chromene, guinoline, isoquinoline, 1,2,3,4-tetrahydroisoquinoline, cinnoline, quinazoline, quinoxaline, phthalazine and benzo-1, 2, 3-triazine.

N—H groups in said heterocyclic rings should where possible be in derivatized form, for example as N-alkyl group.

Where the phenyl nuclei or the heterocyclic rings are substituted, there are preferably two (identical or different) or, in particular, a single substituent.

Examples of alkyl groups carrying unsubstituted or substituted phenylalkyl groups and heterocyclic rings for R are benzyl, 2-phenylethyl, 3-phenyprorpyl, 4-phenylbutyl, o-, m- or p-hydroxylbenzyl, o-, m- or p-carboxylbenzyl, o-, m- or p-sulfobenzyl, o-, m- or p-methoxy or -ethoxycarbonylbenzyl, 2-furylmethyl, N-methyl-4-piperidinylmethyl or 2-, 3- or 4-pyridinylmethyl.

Where phenyl nuclei and heterocyclic rings are substituted, there are preferably groups which confer solubility in water, such as hydroxyl groups, carboxyl groups or sulfo groups.

Examples of said $C_1$–$C_4$-, $C_1$–$C_{12}$- and $C_1$–$C_{20}$-alkyl groups are the appropriate radicals listed above for R.

The crystalline solid prepared according to the invention is particularly suitable as component of solid detergent and cleaner formulations. The present invention therefore also relates to solid detergent and cleaner formulations which comprise the crystalline solid with sufficiently low hygroscopicity prepared according to the invention from glycine-N,N-diacetic acid derivatives I as complexing agent for alkaline earth and heavy metal ions in the amounts customary for this purpose, in addition to other conventional ingredients of such formulations. Compositions and conventional ingredients of such solid detergent and cleaner formulations are known to the skilled worker and therefore need not be illustrated in detail here.

The following Examples are intended to illustrate the invention in detail. The glycine-N,N-diacetic acid derivative I employed in each case was α-alanine-N,N-diacetic acid trisodium salt (methylglycine-N,N-diacetic acid, "MGDA") with a purity of about 80% by weight based on the solids content. Unless stated otherwise, % data always mean % by weight.

EXAMPLE 1

650 g of MGDA solution (water content 60.7%) were evaporated in a laboratory DTB (capacity 0.7 l) at 176° C. under 3 bar to a water content of 20% (based on the total weight). The water-containing melt was cooled to 80° C. and solidified 15 minutes after addition of 20 g of MGDA nuclei. The shaft rotated at 20 rpm. 250 g of crystalline solid were discharged from the DTB, and the solid was still free-flowing and stable on storage under the test conditions (open storage at 25° C. and 76% relative humidity for 200 hours).

EXAMPLE 2

325 g of spray-dried MGDA powder (water content 4.2%) and 128 g of GDA solution (water content 60.7%) were mixed in a laboratory DTB (capacity 0.7 l) and heated to 60° C. The shaft rotated at 20 rpm. The mixture solidified within 10 minutes. 450 g of crystalline solid were obtained and were still free-flowing and stable on storage under the test conditions (open storage at 25° C. and 76% relative humidity for 200 hours).

EXAMPLE 3 a) 14 kg of spray-dried MGDA powder (water content 4%) and 5.5 kg of MGDA solution (water content 60%) were mixed in a cleaned DTB (capacity 30 l) at 8 rpm. The heating jacket of the DTB was heated to 60° C. The mixture solidified within 15 minutes without addition of nuclei. 13.6 kg of crystalline solid were discharged and were still free-flowing and stable on storage under the test conditions (open storage at 25° C. and 76% relative humidity for 200 hours).

b) The test was repeated four times under the same conditions, but the powder and solution were mixed and heated in the uncleaned apparatus. Crystallization then started after only 5 to 10 minutes. The product had in each case the same properties in respect of flowability and storage stability.

Comparative Examples A and B

For comparison, MGDA was spray-dried by conventional methods (A) and spray-dried, compacted and treated with 1% benzoic acid (B). The flowability and storage stability under the test conditions (open storage at 25° C. and 76% relative humidity) were inadequate after only 3 hours for product A and after only 115 hours for product B.

We claim:

1. A process for preparing a crystalline solid which has a sufficiently low hygroscopicity for processing and use and essentially consists of glycine-N,N-diacetic acid derivatives of the formula I

(I)

where
R is methyl, and
M is hydrogen, alkali metal, alkaline earth metal, ammonium or substituted ammonium in the appropriate stoichiometric amounts,
which comprises adjusting the water content of the starting material containing the glycine-N,N-diacetic acid derivatives I to a value of from 10 to 25% by weight, based on the starting material, and subsequently bringing about crystallization under mechanical stress in a mixing, stirring, kneading or extrusion apparatus.

2. A process as claimed in claim 1, wherein the water content of the starting material is adjusted to from 18 to 22% by weight, based on the starting material.

3. A process as claimed in claim 1, wherein the starting material used for the crystallization is produced by adjusting an appropriate aqueous solution of the glycine-N,N-diacetic acid derivatives I to the required water content by distilling off water.

4. A process as claimed in claim 1, wherein the starting material with the required water content used for the crystallization is produced by mixing an appropriate aqueous solution of the glycine-N,N-diacetic acid derivatives I with dehydrated glycine-N,N-diacetic acid derivatives I in the suitable ratio.

5. A process as claimed in claim 1, wherein the starting material with the required water content used for the crystallization is produced by mixing dehydrated glycine-N,N-diacetic acid derivatives I with water in the suitable ratio.

6. A process as claimed in claim 1, wherein the crystallization is carried out at a temperature in the range from 10 to 100° C.

7. A process as claimed in claim 1, wherein the crystallization is speeded up by adding from 0.001 to 50% by weight, based on the amount of glycine-N,N-diacetic acid derivatives I present in the starting material, of crystalline glycine-N,N-diacetic acid derivatives I as crystallization nuclei.

* * * * *